United States Patent [19]
Person et al.

[11] Patent Number: 5,997,552
[45] Date of Patent: Dec. 7, 1999

[54] MENISCAL FASTENER APPLYING DEVICE

[75] Inventors: Wayne C. Person, Newtown; Jo Ann B. Gardella, Norwalk; Marc J. Theroux, Bethel, all of Conn.; Michael Oberlander, Concord, Calif.

[73] Assignee: United States Surgical Corporation, Norwalk, Conn.

[21] Appl. No.: 08/546,573

[22] Filed: Oct. 20, 1995

[51] Int. Cl.$^6$ ................................................. A16B 17/00
[52] U.S. Cl. ........................................... 606/139; 606/143
[58] Field of Search ..................................... 606/139, 142, 606/143, 75, 219; 227/175.1–182.1, 19, 901

[56] References Cited

U.S. PATENT DOCUMENTS

| | | |
|---|---|---|
| 4,410,125 | 10/1983 | Noiles et al. . |
| 4,456,006 | 6/1984 | Wevers et al. . |
| 4,513,746 | 4/1985 | Aranyi et al. . |
| 4,523,707 | 6/1985 | Blake, III et al. . |
| 4,534,351 | 8/1985 | Rothfuss et al. ........................ 606/143 |
| 4,549,545 | 10/1985 | Levy . |
| 4,569,469 | 2/1986 | Mongeon et al. ........................ 606/75 |
| 4,635,637 | 1/1987 | Schreiber . |
| 4,664,304 | 5/1987 | Wendt et al. . |
| 4,696,300 | 9/1987 | Anderson . |
| 4,781,190 | 11/1988 | Lee . |
| 4,873,976 | 10/1989 | Schreiber . |
| 4,895,148 | 1/1990 | Bays et al. . |
| 4,924,865 | 5/1990 | Bays et al. . |
| 4,976,715 | 12/1990 | Bays et al. . |
| 5,002,562 | 3/1991 | Oberlander . |
| 5,037,422 | 8/1991 | Hayhurst et al. . |
| 5,059,206 | 10/1991 | Winters . |
| 5,100,417 | 3/1992 | Cerier et al. . |
| 5,102,421 | 4/1992 | Anspach, Jr. . |
| 5,114,065 | 5/1992 | Storace . |
| 5,141,520 | 8/1992 | Goble et al. . |
| 5,152,765 | 10/1992 | Ross et al. . |
| 5,154,189 | 10/1992 | Oberlander . |
| 5,161,725 | 11/1992 | Murray et al. . |
| 5,192,288 | 3/1993 | Thompson et al. ..................... 606/143 |
| 5,203,784 | 4/1993 | Ross et al. . |
| 5,220,928 | 6/1993 | Oddsen et al. . |
| 5,224,946 | 7/1993 | Hayhurst et al. . |
| 5,236,431 | 8/1993 | Gogolewski et al. . |
| 5,257,713 | 11/1993 | Green et al. . |
| 5,258,010 | 11/1993 | Green et al. . |
| 5,258,016 | 11/1993 | DiPoto et al. . |
| 5,261,914 | 11/1993 | Warren . |
| 5,269,783 | 12/1993 | Sander . |
| 5,328,077 | 7/1994 | Lou ........................................... 606/75 |
| 5,364,400 | 11/1994 | Rego, Jr. et al. . |
| 5,370,662 | 12/1994 | Stone et al. . |
| 5,374,268 | 12/1994 | Sander . |
| 5,423,471 | 6/1995 | Mastri et al. . |

*Primary Examiner*—Michael Powell Buiz
*Assistant Examiner*—Tina T. D. Pham

[57] ABSTRACT

A meniscal fastener applying device for repairing tears in the meniscus of the knee. The device includes a handle assembly and an elongated body portion attached thereto. The handle assembly is operatively attached to a firing mechanism to remotely actuate a firing bar. The firing bar is movably positioned within the elongated body portion to engage and eject a fastener from within the elongated body portion. The elongated body portion includes a support casing which is preferably constructed from stainless steel. The support casing has a cylindrical proximal cross-section that tapers into a distal cross-section having planar top and bottom surfaces. The distal end of the elongated body portion further includes a pair of locator barbs and a tapered distal face.

22 Claims, 15 Drawing Sheets

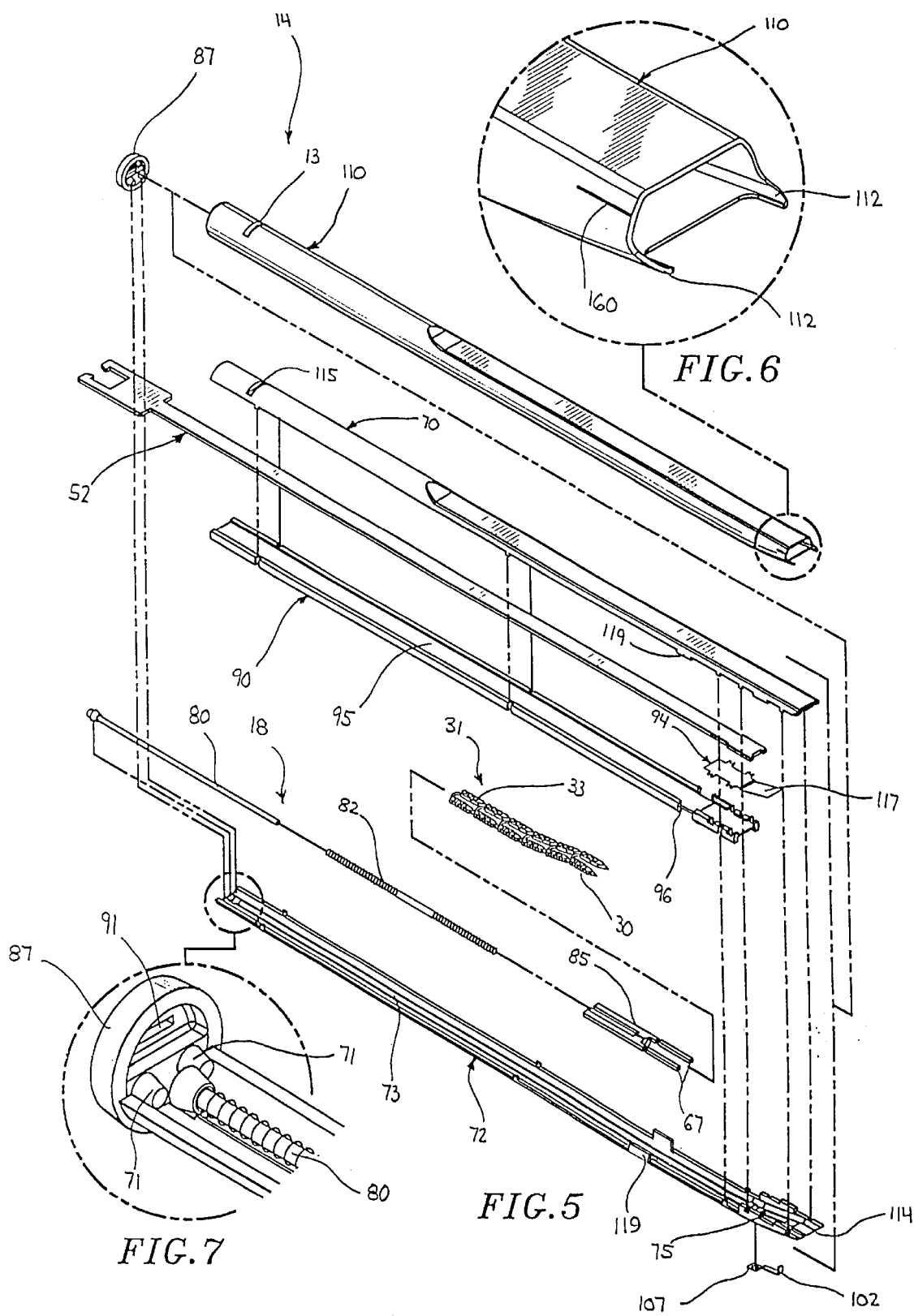

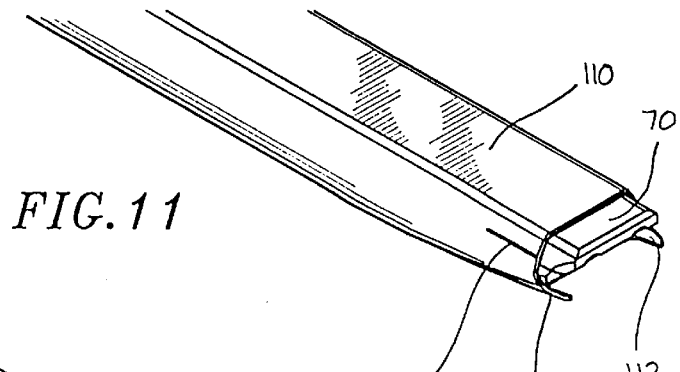
FIG. 11
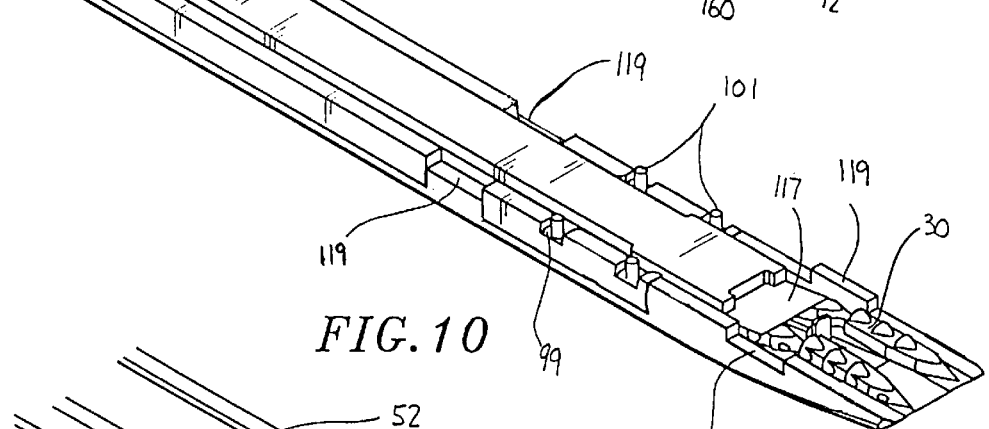
FIG. 10
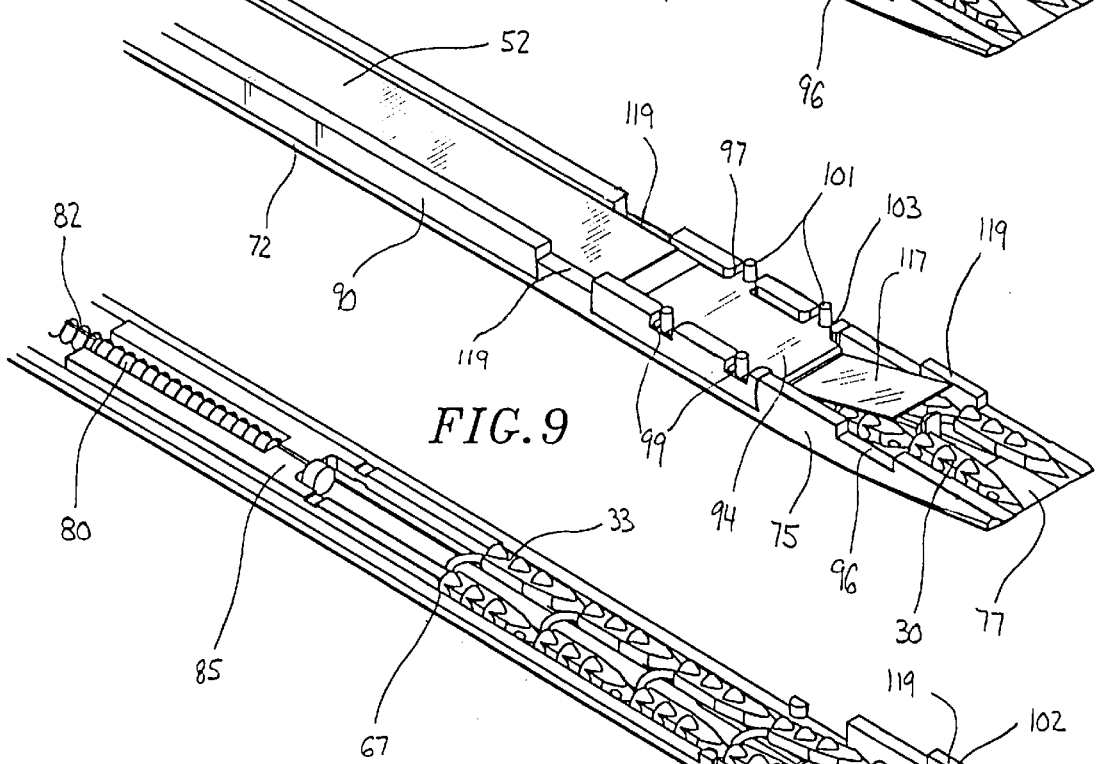
FIG. 9
FIG. 8

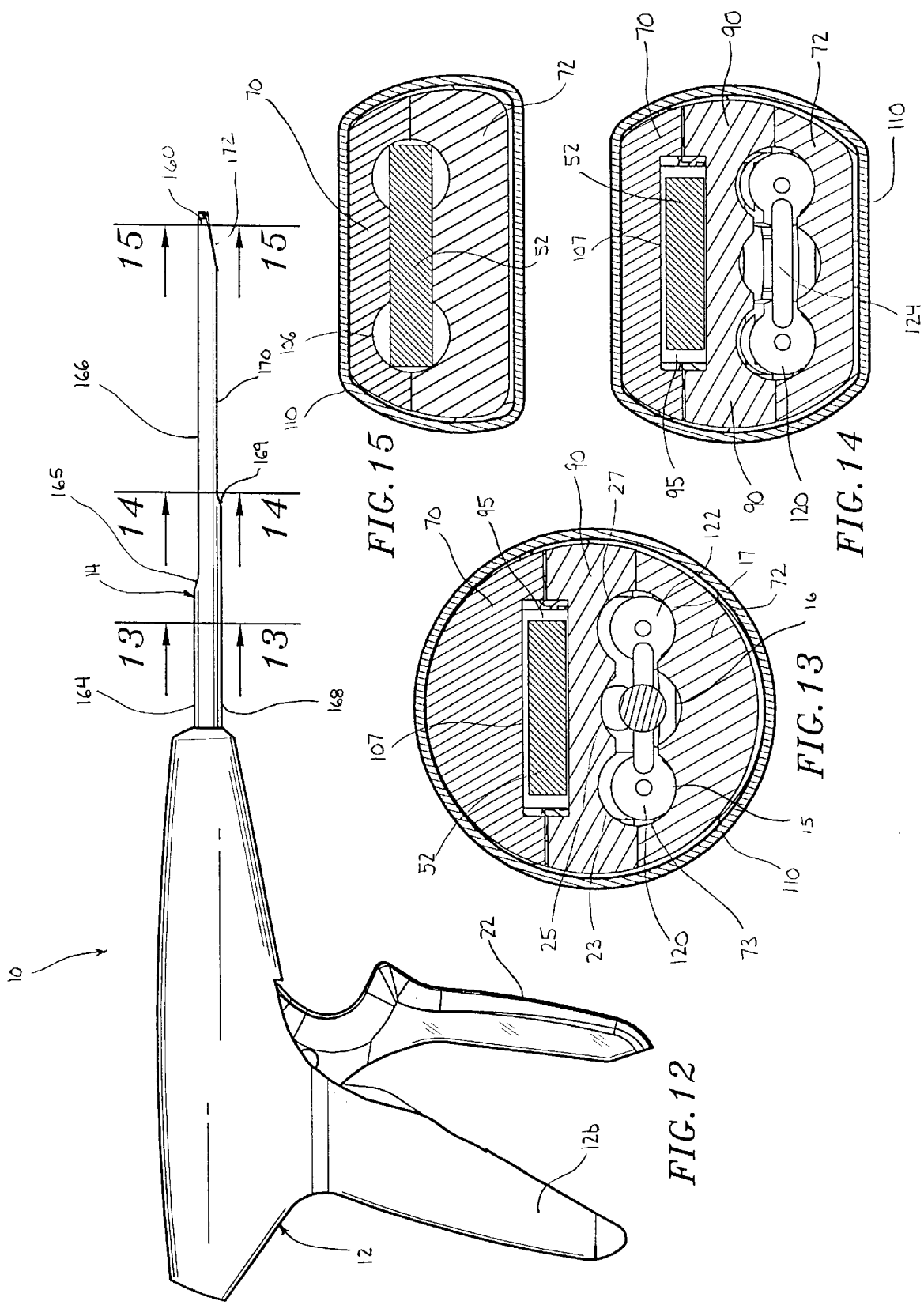

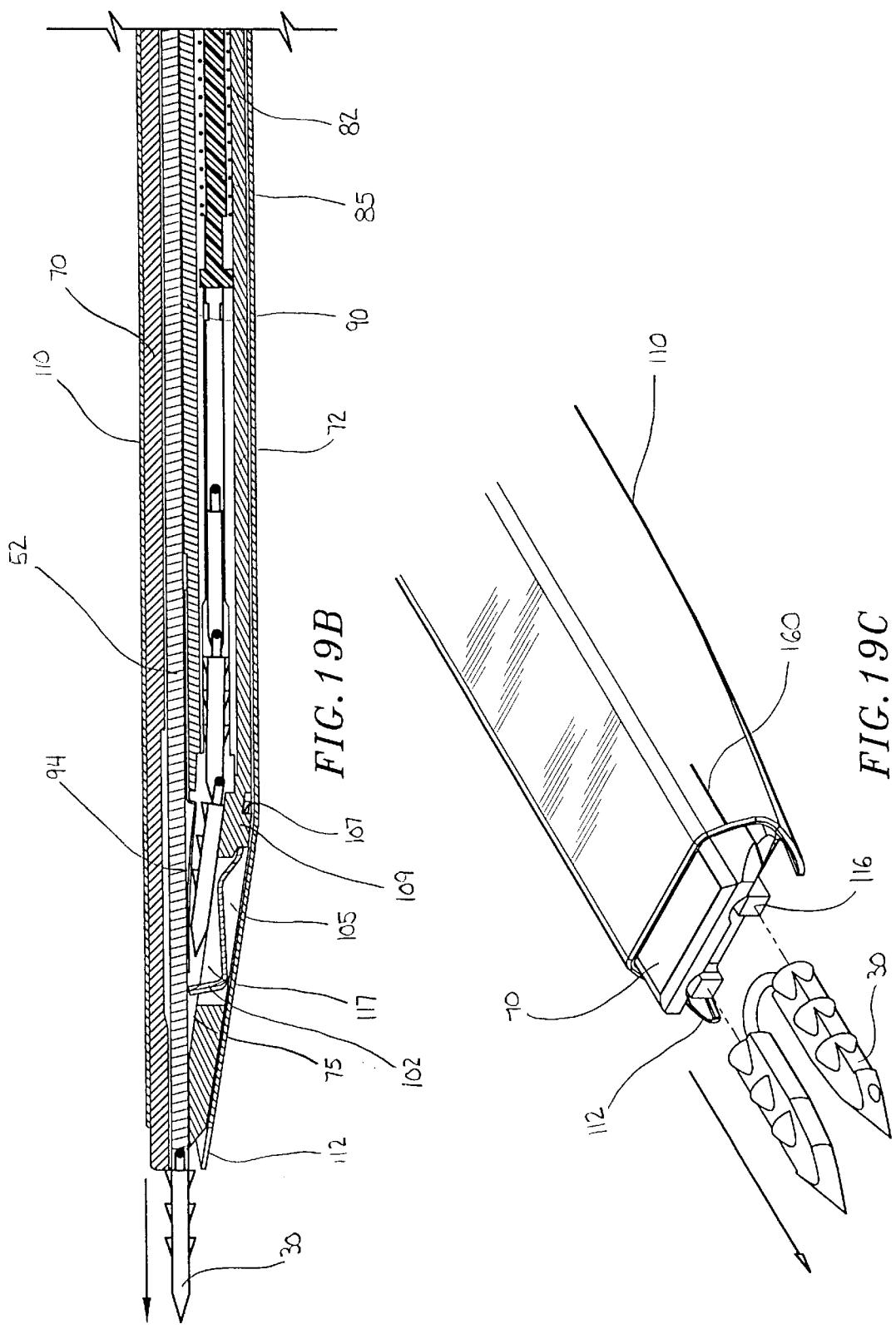

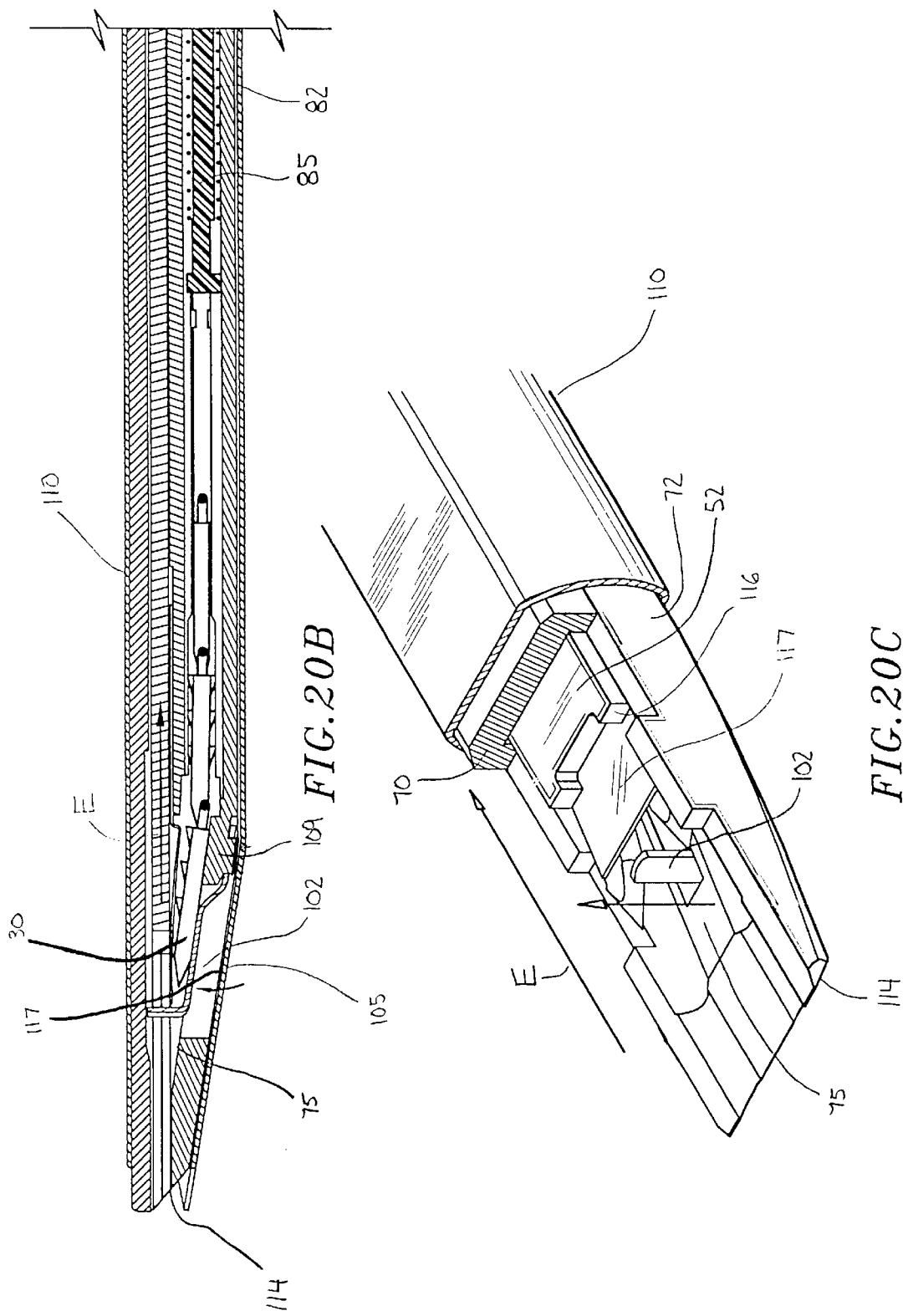

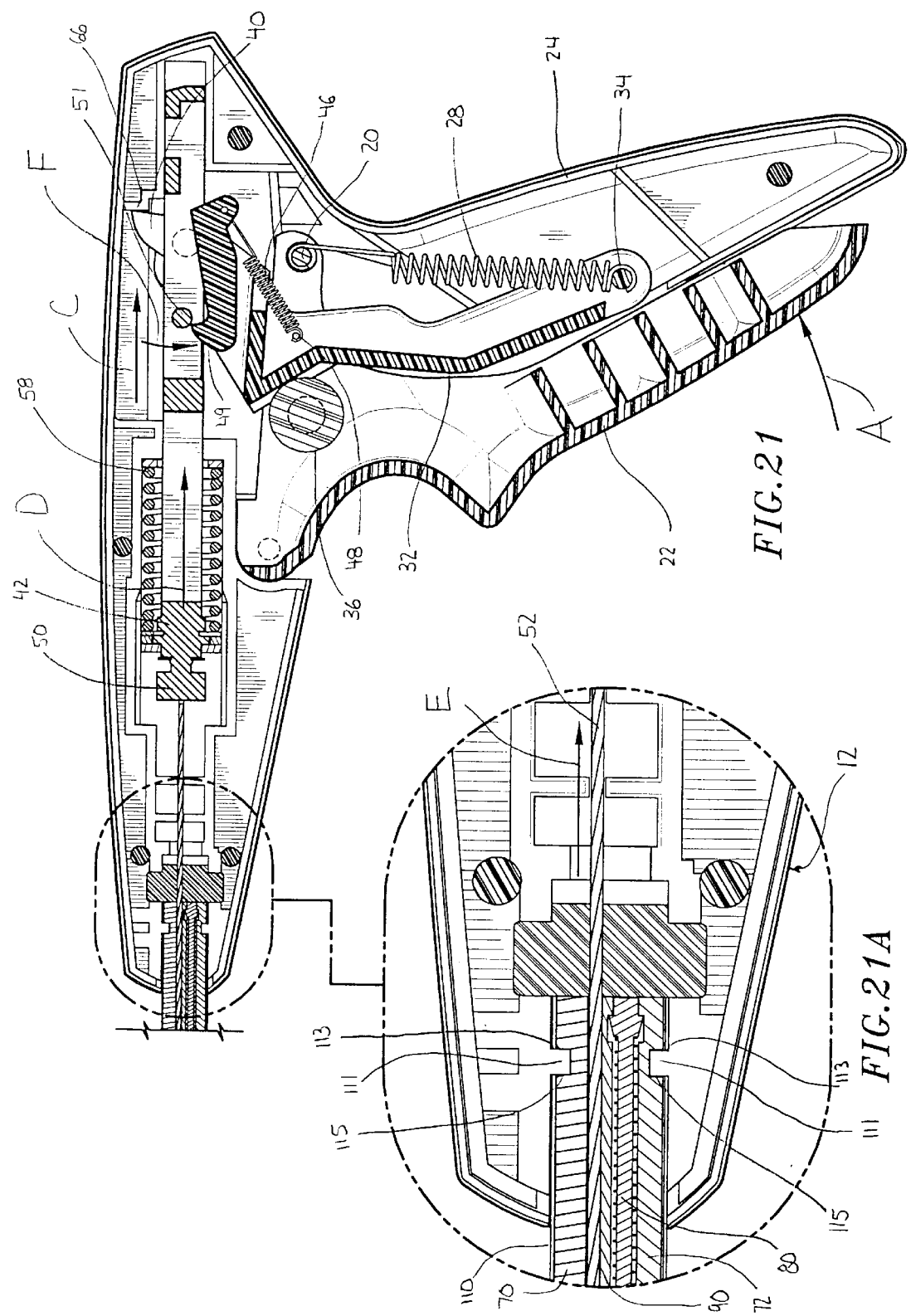

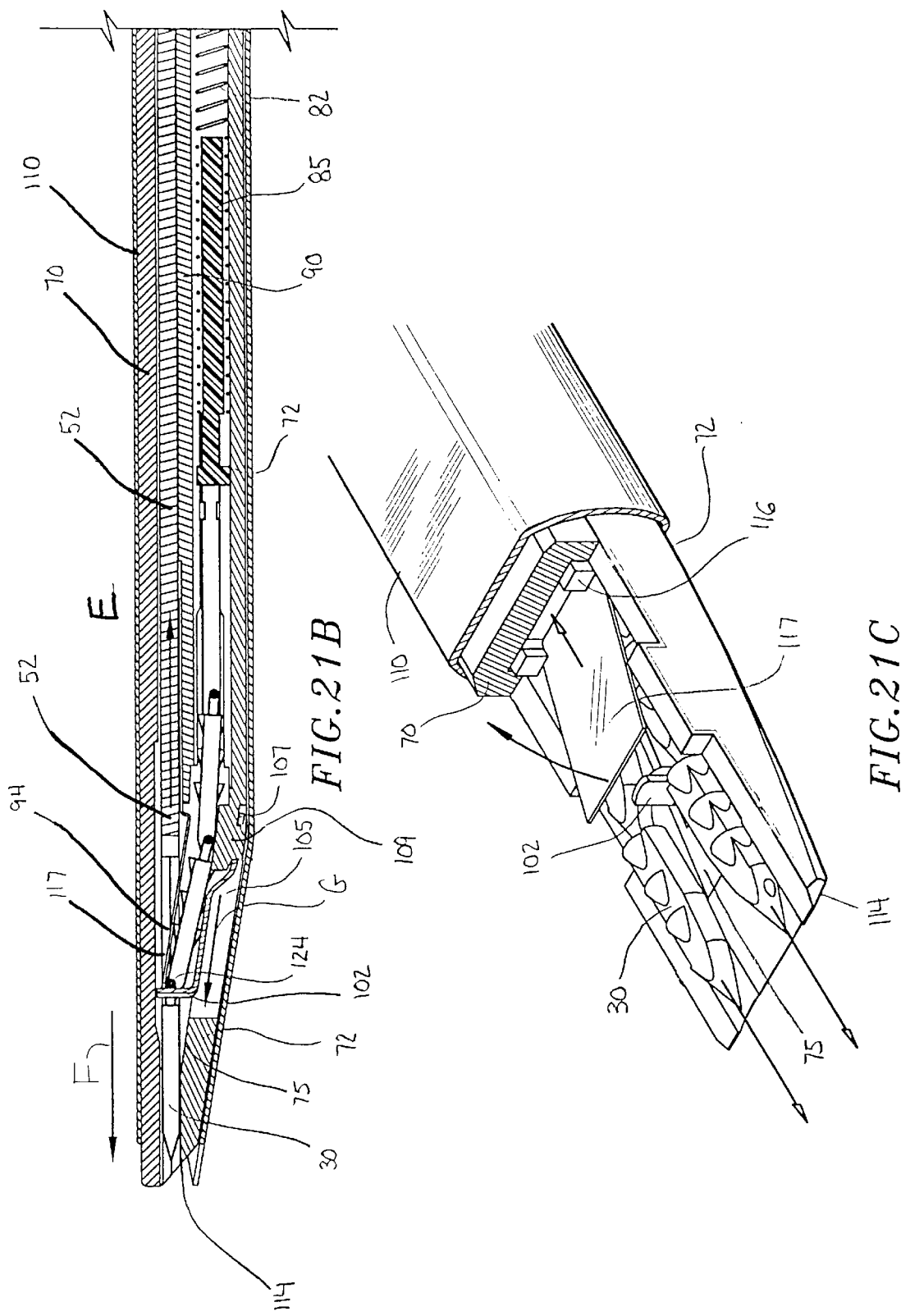

MENISCAL FASTENER APPLYING DEVICE

BACKGROUND

1. Technical Field

The present disclosure relates generally to the field of endoscopic surgical devices. More specifically, the present disclosure relates to an endoscopic fastener applying device for repairing torn tissue such as torn meniscus tissue in the knee.

2. Background of Related Art

A technique has been developed using arthroscopic instruments which provides for meniscal repair through the use of a pair of surgical needles which are inserted through cannuli into the knee on opposite sides of the tear in the meniscus to be repaired. The needles are linked by a single suture which is pushed down through the cannuli and across the tear. An incision is made in the skin at the point where the needles exit the knee joint so that the leading end of each needle may be grasped and pulled through the joint. The ends of the sutures are then grasped after the needles are removed from the suture ends and the suture is then tied so that a horizontal suture is created in the meniscus. This procedure is repeated for placement of as many sutures as necessary to repair the meniscus tear. This process is time consuming, and the strength of the repair is dependent upon the tension created by the knot tied in the suture. There are significant inherent risks of injury to nerves and vascular structures when passing the needles and tying the suture over the nerves and vasculature of the underlying tissue.

An additional procedure and instrument is known from U.S. Pat. No. 5,002,562, in which a barbed clip and an instrument for applying the clip for repairing peripheral meniscal tears is disclosed. The instrument has a pair of opposed arcuate jaws which are shaped to hold a complementary-shaped curved surgical clip therebetween, such that the barbs of the clip are retained within notches in the jaws until the clip is inserted. The legs of the clip are typically joined by a flexible material, such as a suture. The jaws are biased in a normally open position, and as the jaws are pushed into the tissue, the jaws are scissored or closed together until they preferably overlap to move the legs of the clip together until they cross. The jaws are then reopened and backed out of the tissue, with the barbs of the clip retaining the clip in position in the tissue.

SUMMARY

A device is provided which sequentially expels a distal-most meniscal fastener from the distal end of the surgical device and into the meniscus. In particular, the surgical device is provided with a plurality of meniscus fasteners arranged for sequential placement.

The surgical device includes a handle portion having a pivotable handle member with an elongated body portion extending distally from the handle portion. A surgical fastener supply is disposed within the elongated body portion. A firing mechanism is operatively associated with the elongated body portion for firing the distalmost surgical fastener from the device and into the meniscus. The firing mechanism is similar to the firing mechanism disclosed in U.S. Pat. No. 5,285,010, issued Nov. 2, 1993 to Green et al., incorporated herein by reference. An advancing mechanism is operatively associated with the elongated body portion for advancing a surgical fastener from the fastener supply to a firing position in alignment with the firing mechanism. A camming mechanism is operatively associated with the handle portion, and is responsive to a full stroke movement of the pivotable handle member for actuating the firing mechanism.

The elongated body portion of the surgical device further includes a support casing surrounding an inner housing thereof. Preferably, the support casing is constructed of stainless steel and has a configuration that tapers from a generally cylindrical proximal end to a generally rectangular distal end. The strength and configuration of the support casing facilities entry of the distal end of the device into a body joint such as the knee. The distal end of the support casing further includes a pair of barbs or projections which serve the dual function of accurately positioning the distal end of the elongated body portion in relation to the tissue to be repaired and of relocating tissue to be repaired to its proper position prior to making repairs. Fastener locator indicia is also provided at the distal end of the elongated body portion to further aid in positioning the device prior to making repairs.

In a preferred embodiment, the distal end of the inner housing of the elongated body portion is provided with a tapered distal face and is dimensioned to extend from the distal end of the support casing. The tapered distal face of the inner housing is configured to approximate the slope of the superior surface of the menisci such that, when in use, the distal face of the device abuts the tissue to be repaired prior to firing a fastener into the tissue. The configuration enables the firing mechanism to securely insert a fastener into body tissue to be repaired.

BRIEF DESCRIPTION OF THE DRAWINGS

Various embodiments are described herein with reference to the drawings, wherein:

FIG. 5 is a perspective view with parts separated of the elongated body portion of the embodiment shown in FIG. 1;

FIG. 6 is an enlarged view of the distal end of the elongated body portion of the device shown in the indicated area of detail of FIG. 5;

FIG. 7 is an enlarged view of the proximal end of the elongated body portion of the device shown in the indicated area of detail of FIG. 5;

FIG. 8 is a perspective view of the distal end of the lower housing half of the elongated body portion of the embodiment shown in FIG. 1;

FIG. 9 is a perspective view of the distal end of the lower housing half and cover plate of the elongated body portion of the embodiment shown in FIG. 1;

FIG. 10 is a perspective view of the distal end of the lower housing half, cover plate, and firing bar of the elongated body portion of the embodiment shown in FIG. 1;

FIG. 11 is a perspective view of the distal end of the elongated body portion of the embodiment shown in FIG. 1;

FIG. 12 is a side elevational view of the embodiment shown in FIG. 1;

FIG. 13 is a cross-sectional view taken along section line 13—13 of FIG. 12;

FIG. 14 is a cross-sectional view taken along section line 14—14 of FIG. 12;

FIG. 15 is a cross-sectional view taken along section line 15—15 of FIG. 12;

FIG. 19B is a side cross-sectional view of the distal end of the elongated body portion of the device in a post-fired condition;

FIG. 19C is a perspective view of the distal end of the elongated body portion of the device shown in FIG. 19B;

FIG. 20B is a side cross-sectional view of the distal end of the elongated body portion of the device shown in FIG. 1 in a partially actuated position;

FIG. 20C is a perspective view, partially in section, of the distal end of the elongated body portion of the device shown in FIG. 20B;

FIG. 21 is a side cross-sectional view of the proximal end of the embodiment of the device shown in FIG. 1 in a fully actuated position;

FIG. 21A is an enlarged view of the indicated area of detail of FIG. 21;

FIG. 21B is a side cross-sectional view of the distal end of the elongated body portion of the device shown in FIG. 21;

FIG. 21C is a perspective view, partially in section, of the distal end of the elongated body portion of the device shown in FIG. 21B;

DETAILED DESCRIPTION OF PREFERRED EMBODIMENTS

Figure 1:
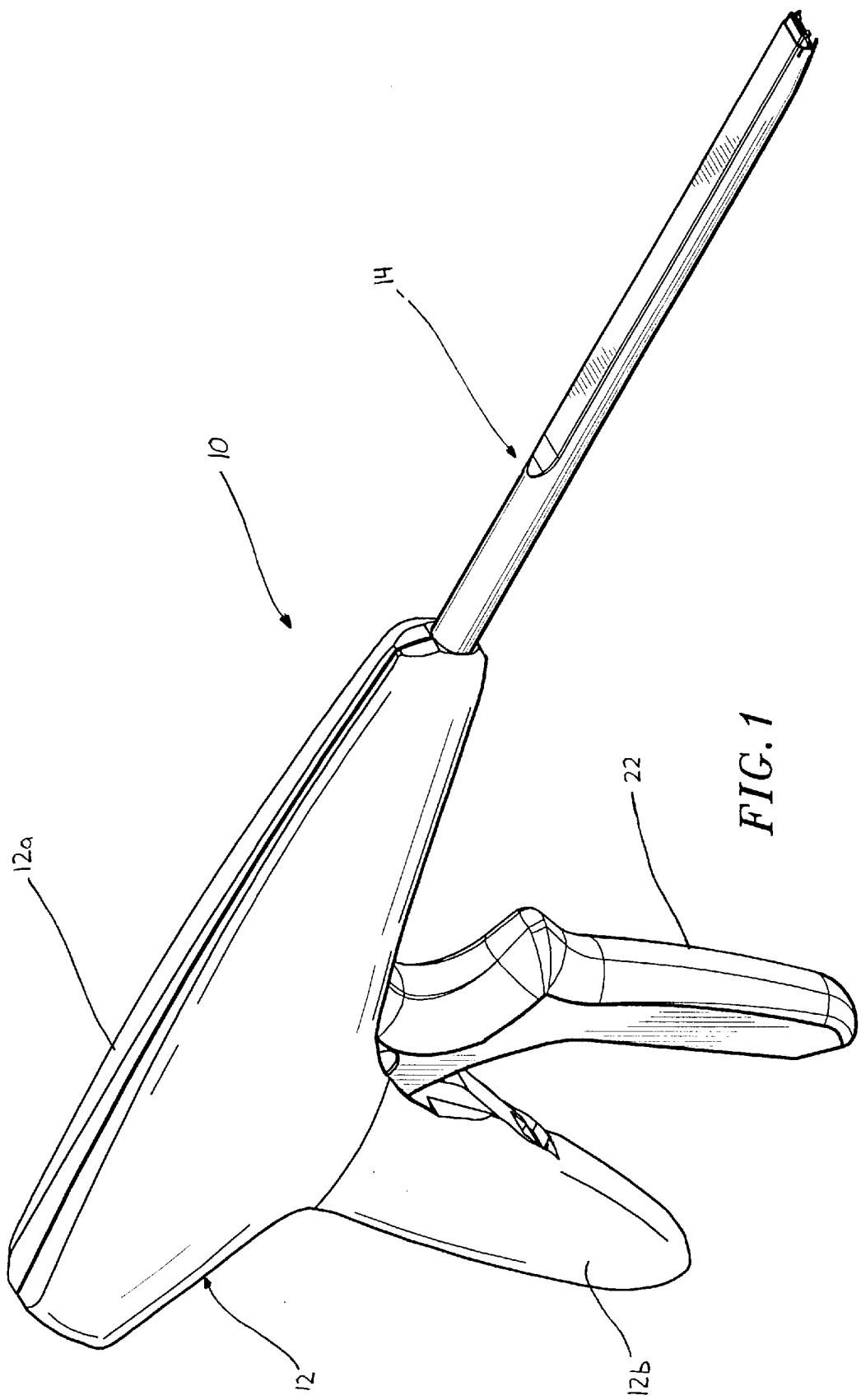
FIG. 1 is a perspective view of one embodiment of the meniscal fastener device of the present disclosure.

Preferred embodiments of the presently disclosed stapler will now be described in detail with reference to the drawings, in which like reference numerals designate identical or corresponding elements in each of the several views.

Referring now to the drawings, FIG. 1 illustrates a first embodiment of the fastener applying device shown generally as 10. Briefly, the staple applying device 10 includes a handle assembly 12 and an elongated body portion 14 defining a longitudinal axis thereof. The elongated body portion 14 is preferably dimensioned for arthroscopic utilization.

Figure 2:
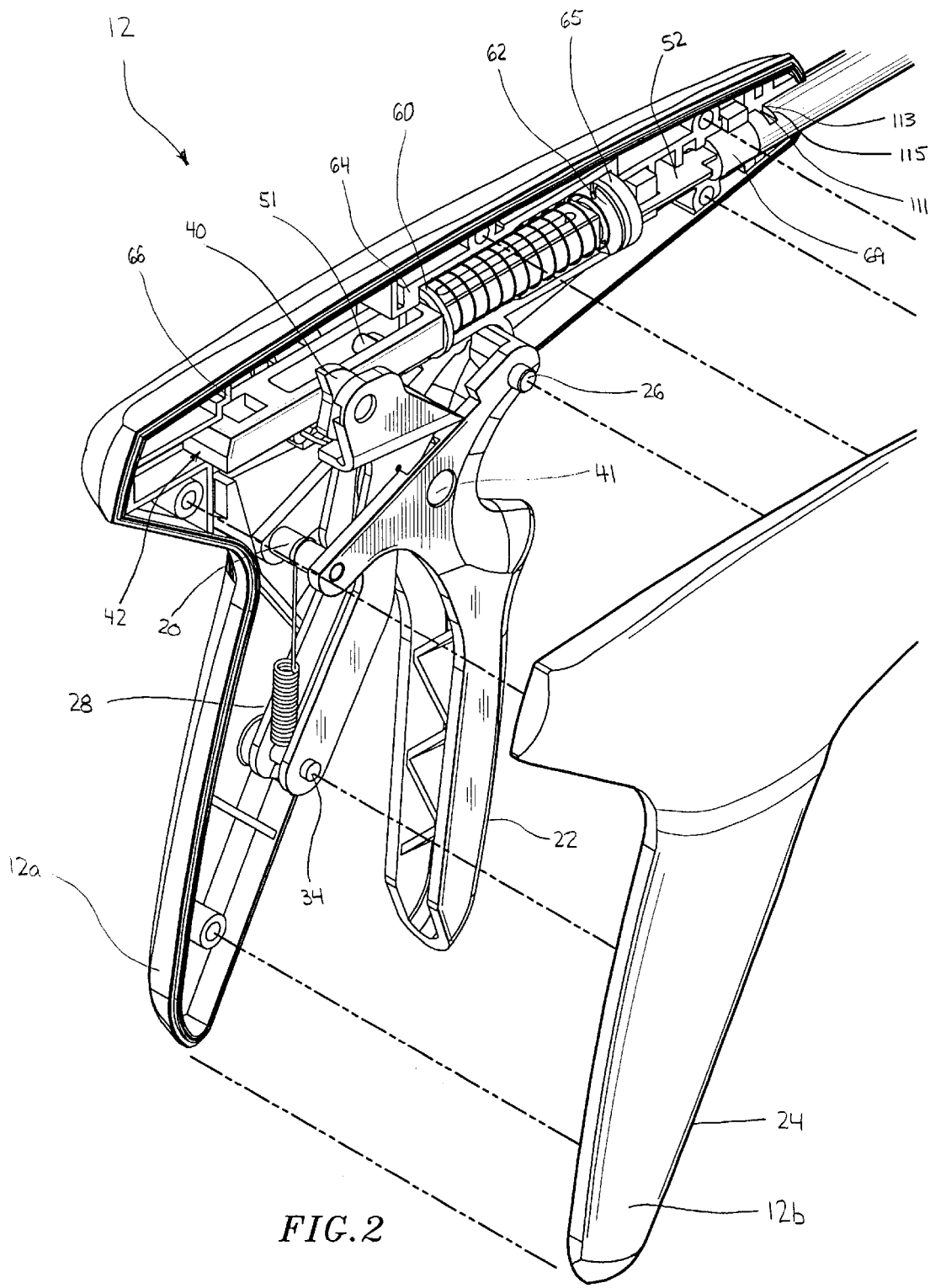
FIG. 2 is a perspective view with parts separated of the handle assembly of the embodiment shown in FIG. 1.
Figure 3:
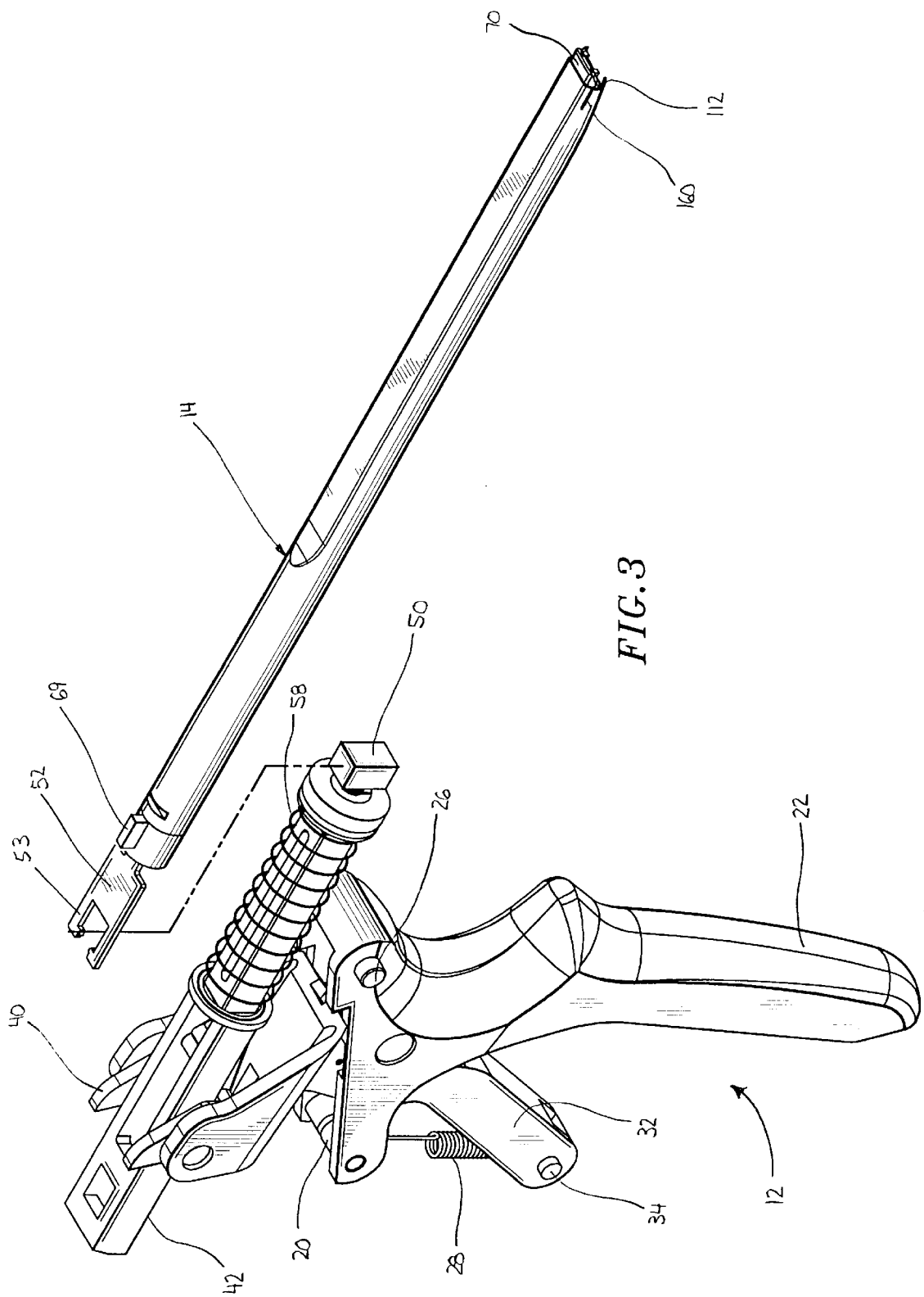
FIG. 3 is a perspective view of the meniscal fastener device of the embodiment shown in FIG. 1 with the handle assembly housing removed and partial separation of parts.

The components of the handle assembly 12 of the fastener applying device 10 are best illustrated in FIGS. 2 and 3. The handle assembly 12 includes a housing formed from molded housing half-sections 12a and 12b within which the components of the handle assembly 12 are positioned. The handle assembly 12 further includes a movable handle 22 and a stationary handle 24 which is formed from portions extending from housing half-sections 12a and 12b to form a pistol grip type handle. Movable handle 22 and stationary handle 24 facilitate remote actuation of a firing bar 52 through the elongated body portion 14 to effect the ejection of a surgical fastener 30 (FIG. 5) from the distal end of the elongated body portion 14.

Figure 4:
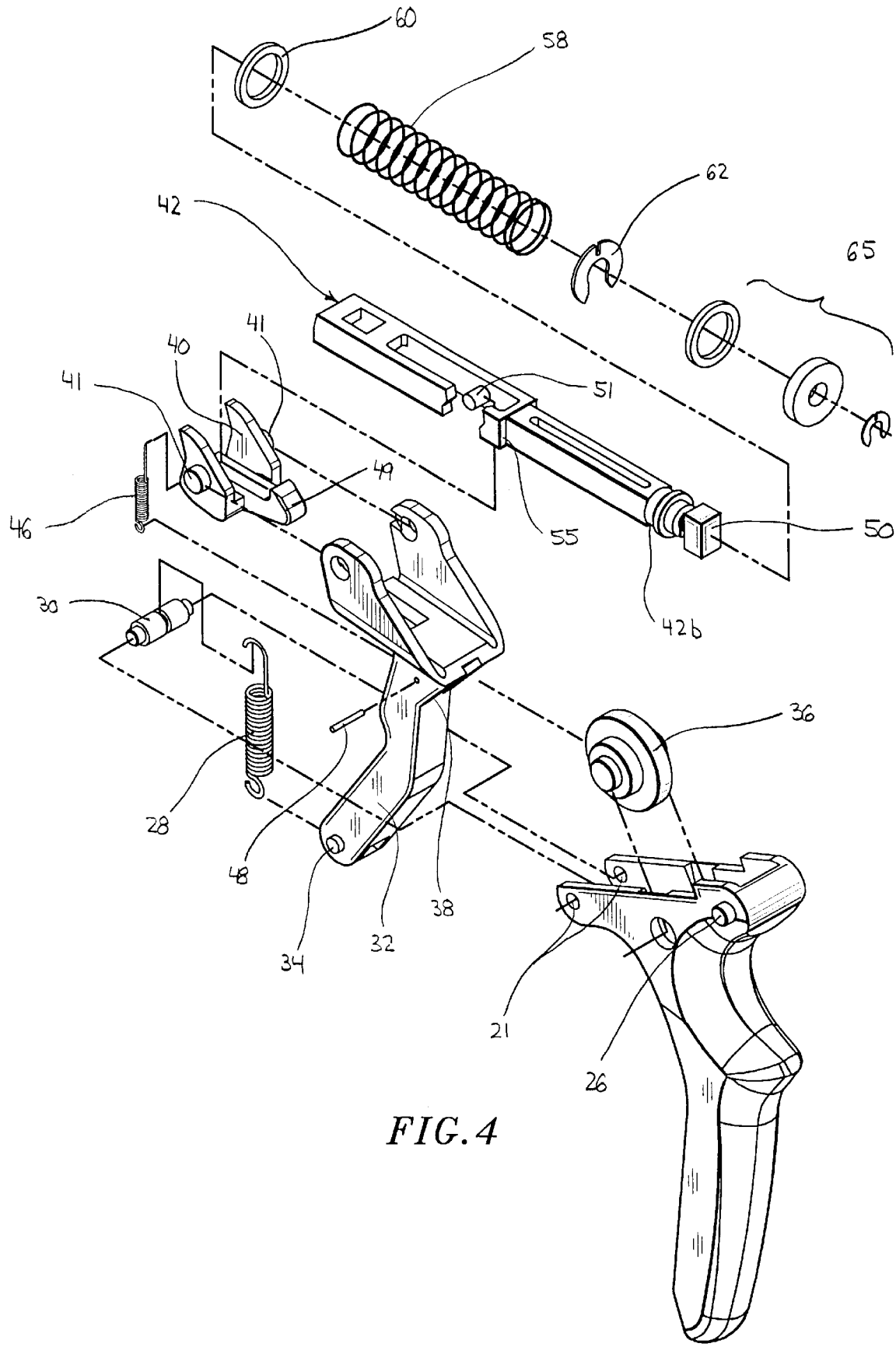
FIG. 4 is a perspective view of the handle assembly with parts separated and in partial section, of the embodiment shown in FIG. 1 with the handle assembly housing removed.

Referring now to FIGS. 2–4, the movable handle member 22 is secured to the housing half sections 12a and 12b by a pin 26 which permits rotation of the movable handle 22 relative to the stationary handle 12. A handle spring 28 is connected to the movable handle 22 by a pin 20 and to the housing 12 by a pin 34 so as to bias the movable handle 22 to an open position. The pin 20 is dimensioned to be received in openings 21 formed in the movable handle 22.

An actuation arm member 32 is operatively associated with the movable handle 22 and is pivotably connected to the lower end of the stationary handle 24 by pin 34. A cam roller member 36 is rotatably mounted to the movable handle 22 and is configured to engage and move along a cam path surface 38 defined on the actuation arm member 32 by the proximal facing outer surface thereof. Engagement between the cam roller member 36 and the cam path surface 38 effectuates counter-clockwise rotation of the actuation arm member 32 about pin 34 when the instrument is viewed from the right side, as shown in FIG. 2.

A latch member 40 is pivotably mounted to the top portion of the actuation arm 32 by pivot members 41. The latch member 40 is dimensioned and configured to detachably engage with a firing block 42 (shown in partial section in FIG. 4) which is slidably mounted in the handle assembly 12. An engaging spring 46 connects the latch member 40 to the actuation arm member 32 through pin 48 so as to pivot the latch member 40 about pivot members 41 into engagement with the firing block 42. The latch member 40 has a hook member 49 pivotable about pivot members 41 into engagement with a post 51 formed on the firing block 42.

As mentioned above, the firing block 42 is slidably mounted in the handle assembly 12 and is movable in response to corresponding movement of the movable handle member 22. A mounting projection 50 extends from the end of the firing block 42 and is dimensioned and configured so as to detachably engage with the proximal end 53 of elongated firing bar 52 (FIG. 3).

Referring again to FIG. 4, a bearing washer 60 is received about and engages a central portion 55 of the firing block 42, and a snap washer 62 is fixedly attached to the distal end portion 42b of the firing block 42 to capture and retain a compression spring 58 therebetween. Upon actuation of the handle assembly, the compression spring 58 is compressed between bearing washer 60 and snap washer 62 creating a force urging firing block 42 in a distal direction. Additional washers 65 for sealing, spacing and fitting purposes may be operatively associated with the distal end portion 42b of the firing block 42.

As described above, proximal movement of the movable handle 22 causes the cam roller 36 to engage the cam path surface 38 and rotate actuating arm member 32 and latch member 40 in a counter-clockwise direction when viewing the instrument from the right side, as shown in FIG. 2. The hook member 49 formed on the latch member 40 engages post 51 formed on the firing block 42 to slide the firing block 42 proximally as latch member 40 and actuating cam member 32 rotate counter clockwise in response to proximal movement of handle 22. The proximal movement of the firing block 42 causes bearing washer 60 to engage a bearing surface 64 defined on the interior of the handle assembly 12 (See FIG. 2). As the firing block 42 is moved proximally, the compression spring 58 is compressed between the washer 60 and the snap washer 62 creating a force urging firing block 42 in a distal direction. After the spring 58 has been compressed, the latch member 40 contacts a camming wall 66, shown in FIGS. 2 and 21, defined in the proximal end portion of the handle assembly 12 which, in turn, causes the latch member 40 to pivot clockwise about members 41 to disengage hook member 49 from post 51. The release of stored energy from the compression spring 58 urges the firing block 42 to move distally resulting in corresponding distal movement of the firing bar 52. After the firing block 42 has moved along its full distal path of travel within the handle assembly 12 and the movable handle 22 is returned to its rest position by handle spring 28, the hook 49 of the latch member 40 is returned to a position detachably engaging the post 51 of the firing block 42.

FIGS. 5–7 illustrate the elongated body portion 14 of the fastener applying device 10. Body portion 14 includes an upper housing half-section 70 and a lower housing half-section 72, a series of fasteners 31 arranged in tip to tail fashion, and a mechanism which facilitates advancing the series of fasteners 31 towards a distal end of the body portion 14 and subsequently firing the distalmost surgical fastener 30 from the distal end of the body portion 14 into body tissue, such as the meniscus of a human joint.

The series of fasteners 31 is slidably disposed in an elongated track 73 defined in the lower housing half-section 72 of the elongated body portion 14. Referring temporarily to FIGS. 13–15, the elongated track 73 includes three spaced longitudinal grooves 15, 16 and 17 which extend along the length of the body portion 14 and help to align the fasteners 31 as they advance distally within the body portion 14. Referring again to FIG. 5, an advancing mechanism 18 is slidably positioned proximal to the series of fasteners 31 on the elongated track 73. The preferred advancing mechanism 18 includes a fastener follower 85 having a pair of distal legs 67 which engage the proximal-most fastener 33 in the series of fasteners 31. The advancing mechanism 18 further includes a follower spring 82 and a follower rod 80 which engage and urge the fastener follower 85 distally to urge the series of fasteners 31 distally along elongated track 73. In one embodiment, the proximal end of the follower rod 80 may be secured in a recess defined by lower housing 72 and cover plate 90 (see FIG. 19A).

In another embodiment, a cap seal 87, as best seen in FIG. 7, may be provided and positioned at the proximal end of the elongated body portion 14. The cap seal 87 includes a rectangular longitudinal slot 91 which permits passage of the proximal end of the firing bar 52 into the handle assembly 12. A pair of distally protruding nubs 71 are configured to be received in the proximal ends of the longitudinally extending grooves 15 and 17 formed in the track 73 to align the cap seal 87 in relation to the lower housing half-section 72.

The distal end of the lower housing half-section 72 includes a ramped surface 75 (also shown in FIG. 19B), that is upwardly tapered in a distal direction toward the central longitudinal axis of the device and the upper housing half-section 70. At a distal end, the inner wall of the ramped surface 75 extends along an axis substantially parallel to the longitudinal axis of the elongated body portion 14. The significance of the ramped surface 75 will be discussed in further detail below.

A cover plate 90 is configured to be positioned in nested arrangement above the lower housing half-section 72 of the elongated body portion 14. The cover plate 90 extends distally to a position adjacent the proximal end of ramped surface 75. Referring temporarily once again to FIGS. 13 to 15, the cover plate 90 has a bottom surface having three spaced longitudinal grooves 23, 25 and 27 in alignment with the longitudinal grooves 15, 16 and 17 formed in the lower housing half-section 72 to define the upper surface of the elongated track 73. The upper surface of the cover plate 90 defines a track 95 which extends along a longitudinal axis of the fastener applying device 10, and is configured for slidable reception of the firing bar 52.

Referring now to FIGS. 8 to 11, an elongated leaf spring 94 is provided at the distal end of the elongated body 14. The leaf spring 94 is provided with tabs 97 configured to be received in recesses 99 formed in the distal end of the cover plate 90. Each of the recesses 99 includes a post 101 which is configured to engage a notch 103 provided in each of the tabs 97 to align and secure the leaf spring 94 in relation to the body portion 14. The proximal end of the leaf spring 94 is positioned in a shallow recess (not shown) formed in the distal end of the cover plate 90 such that the top of the leaf spring 94 is flush with the top of the cover plate 90 and does not obstruct the reciprocating longitudinal path of travel of the firing bar 52 along the track 95 in the cover plate 90. The distal end 117 of the leaf spring 94 overhangs the distal end of the cover plate 90 and is positioned to be engaged by the firing bar 52 and deflected to obstruct the path of travel of a fastener located on the ramped surface 75 when the firing bar 52 has been moved distally.

Referring temporarily to FIG. 19B, an escapement in the form of a fastener retainer 102 is positioned in a recess 105 provided along the centerline of the ramped surface 75. To mount the fastener retainer 102 within the recess 105, the fastener retainer 102 is provided with an opening 107 in its proximal end configured to receive a projection 109 extending from the bottom of the lower housing half-section 72. The distal end of the retainer 102 is resilient and is angled upwardly to obstruct the path of travel of the distalmost fastener and hence the fastener supply 31 when the firing bar 52 is in a retracted position.

Referring once again to FIG. 5, the lower housing half-section 72, the upper housing half-section 70 and the cover plate 90 are provided with tabs 119 and grooves 96 to secure the components of the device together in nested arrangement. Although tabs and grooves are shown, other known means may be used to attach the components of the device together, such as adhesives, screws, or ultrasonic welding. The lower housing half-section 72 is provided with a distal face 114, best seen in FIG. 20B, tapered to approximate the slope of the superior surface of the menisci. Distal face 114 should be tapered approximately 35–45°. The advantage of this configuration will be discussed below. The inner surface 107 of the upper housing half-section 70 defines the upper wall of channel 95 through which the firing bar 52 is reciprocated (See FIGS. 13–15).

Figures 19, 19A:
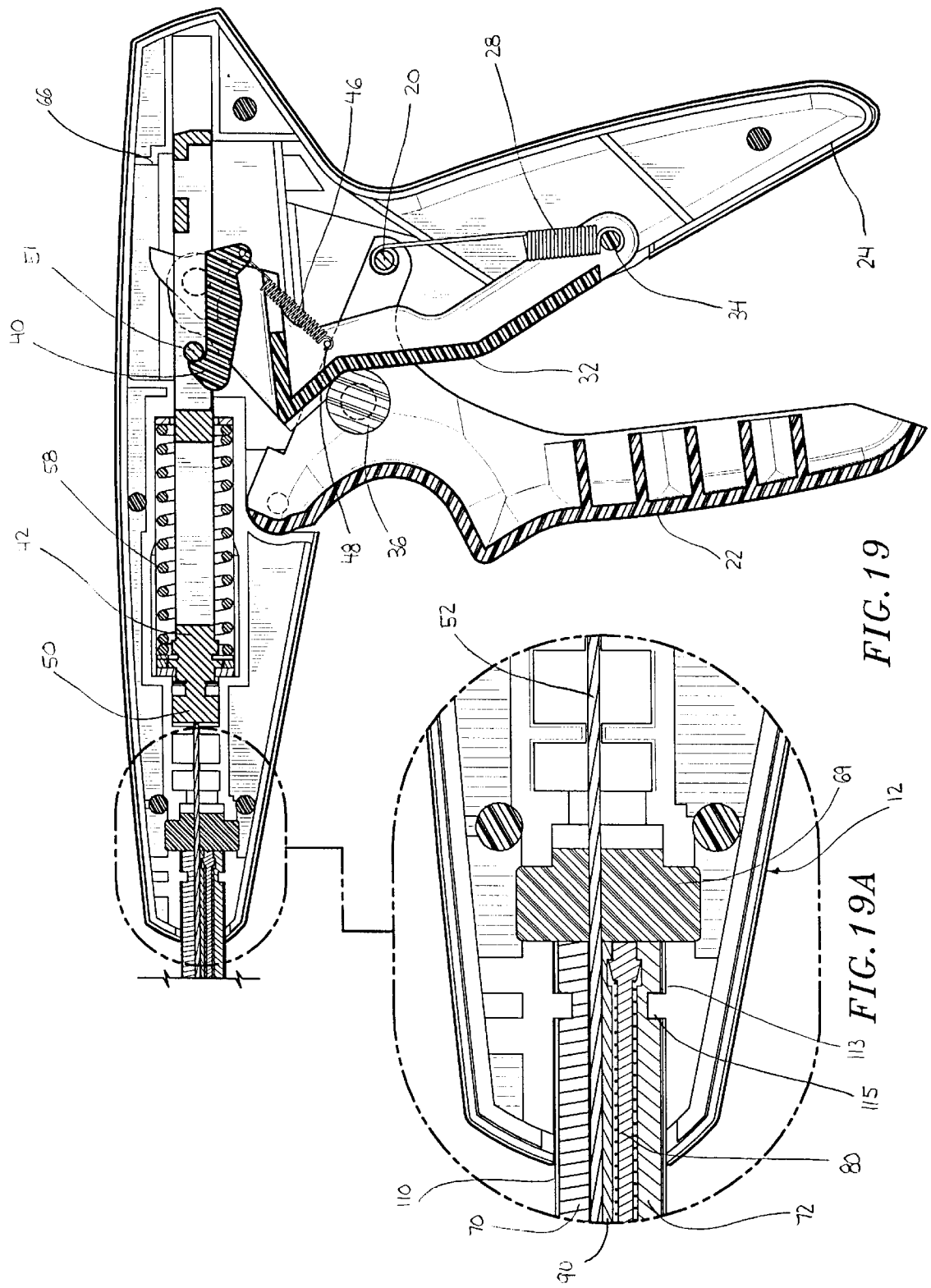
FIG. 19 is a side cross-sectional view of the proximal end of the embodiment shown in FIG. 1 in a post-fired condition.
FIG. 19A is an enlarged view of the indicated area of detail of FIG. 19.

Referring to FIGS. 5 and 6, and temporarily to FIG. 19A, the housing defined by half-sections 70 and 72 is positioned within a support casing 110. Preferably, support casing 110 is constructed of stainless steel although other materials having similar properties and which are suitable for endoscopic use may be utilized. A pair of projections 111, formed in the handle assembly 12, engage in slots 113 and 115 provided in the support casing 110 and the upper and lower housing half-sections 70 and 72, respectively, to mount the elongated body portion 14 to the handle assembly 12 and to secure the support casing 110 in relation to the upper and lower housing half-sections 70 and 72. Referring now to FIGS. 11 to 15, the elongated body portion 14 tapers from a generally cylindrical cross-section near the proximal end to a distal cross-section having planar top and bottom surfaces. The more compact distal cross-section is advantageous in that it facilitates entry of the distal end of the device into a joint capsule, such as the knee. The increased strength of the device provided by the stainless steel support casing 110 further enables the device to be used to pry into the joint capsule without the risk of misaligning the internal components of the device 10.

In order to provide elongated body portion 14 with sufficient strength to enter a joint capsule, certain parameters should be used in the design of the support casing 110. Referring to FIG. 15, the overall length of the support casing 110 should be between about 5.75 and about 6.25 inches. Upper cylindrical section 164 should preferably extend distally about 1.75 to about 2.25 inches into a first transition region tapered at an angle of approximately 12° to 18°. Upper flat 166 extends approximately 3.5 to 4.0 inches from the first transition region 165 to the distal end of the elongated body portion 14. The lower cylindrical section 168 preferably extends distally approximately 2.5 to 3.0 inches to a second transition region 169, also tapered to an angle of approximately 12° to 18°. Lower flat 170 should extend distally about 2.25 to about 2.75 inches from the lower transition region 169 towards the distal end of the device 10. In this embodiment, lower distal end portion 172 is tapered at an angle of approximately 9° towards the distal end of the device.

A pair of barbs 112 are provided at the distal end of the support casing 110 and extend distally approximately 0.07–0.08 inches from the lower surface of the support casing 110. The barbs 112 are positioned to engage the meniscus to locate the fastener applying device 10 and prevent relative movement between the device 10 and the tissue to be mended during actuation of the device 10. The barbs 112 also can be used to reposition tissue within the joint capsule prior to actuating the device.

Fastener locator indicia 160 may be placed on the distal end of the support casing 110 to identify the point of the device from which the fasteners 30 are ejected to facilitate accurate positioning of the device. The indicia 160 may be etched, painted, or crimped to casing 110 and should be of sufficient size to permit easy identification.

Figure 16:
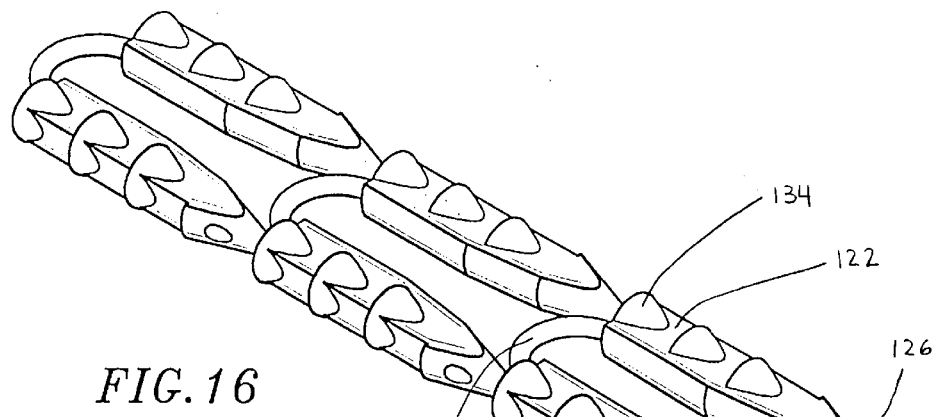
FIG. 16 is a front perspective view of a series of fasteners of the device shown in FIG. 5.
Figure 17:
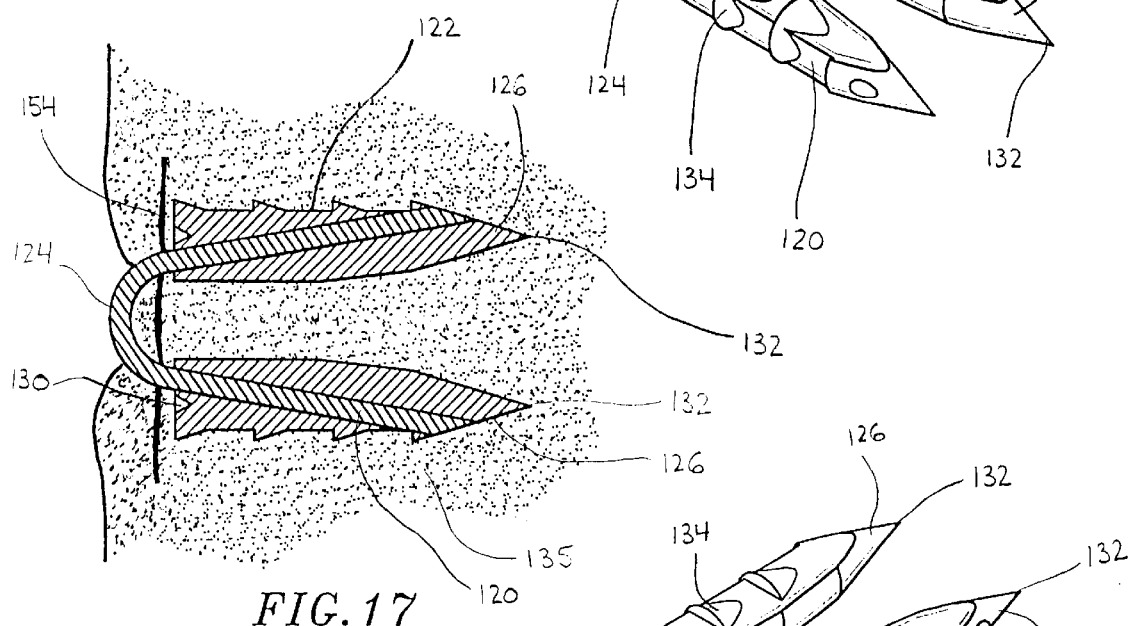
FIG. 17 is a side cross-sectional view of a fastener of the device anchored into body tissue.
Figure 18:
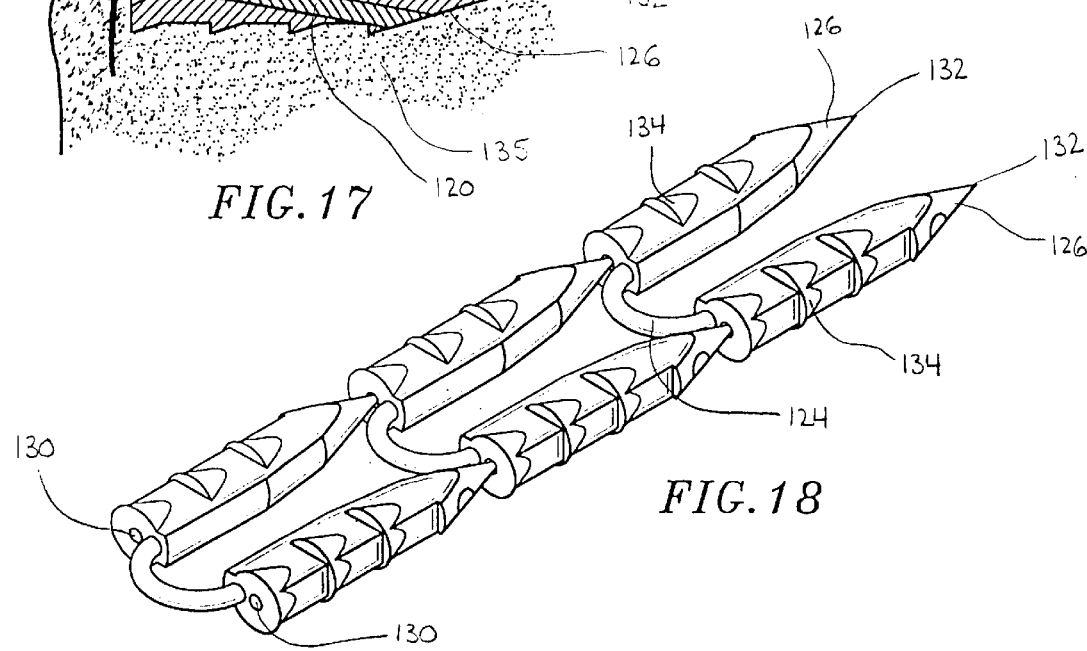
FIG. 18 is a rear perspective view of the series of fasteners shown in FIG. 16.

As illustrated in FIGS. 16 to 18, each fastener in the series of fasteners 31 includes a pair of bioabsorbable anchor members 120 and 122 linked by a flexible bioabsorbable member, such as a suture 124. The anchor members 120 and 122 and suture 124 are preferably selected from material which resorbs at an appropriate rate to facilitate healing of a tear in the meniscus. Each of the anchor members 120 and 122 is provided with a conically tapered distal end 126 and a substantially planar proximal end 128 having a notch 130 formed therein. The notch 130 is configured to receive the distal tip 132 of the fastener anchor member positioned directly proximal to the respective anchoring member when the series of fasteners 31 are positioned on track 73. The flexible member 124 joins the proximal ends of anchor members 120 and 122 at an inner periphery thereof, so as not to interfere with engagement between the follower legs 67 of the advancing mechanism and the anchor member proximal end outer periphery. Each anchor member 120 and 122 is further provided with a series of angled projections 134 to prevent withdrawal of the anchor members 120 and 122 after they have been positioned within body tissue 135.

The operation of the fastener applying device 10 will now be described with reference to FIGS. 19 to 21. FIGS. 19 to 19C illustrate the device in the post-fired position with movable handle 22 returned to a rest position by handle spring 28. Compression spring 58 is extended to move firing block 42 to its distal-most position within the handle assembly 12 and correspondingly to move the firing bar 52 to its distal-most position within the body portion 14. As shown in FIG. 19, the latch member 40 is biased by engaging spring 46 into engagement with post 51 of firing block 42.

As illustrated in FIGS. 19B and 19C, the firing bar 52 in its distal-most position engages the elongated leaf spring 94 causing the distal end of the leaf spring 94 to be deflected toward the fastener positioned on the lower portion of ramp 75 to prevent further distal movement of the series of fasteners 31. The fastener retainer 102 engages the suture portion of the distal-most fastener to restrain the fasteners when leaf spring 94 is not deflected toward the fasteners (See FIG. 8). Fastener retainer 102 is also engaged by and deflected from within the path of travel of the distal-most fastener 30 by the firing bar 52 in its distal-most position. The distal end of the firing bar 52 is provided with a pair of tabs 116 which engage the proximal end of the distal-most fastener 30 to effect ejection of the fastener 30.

Figures 20, 20A:
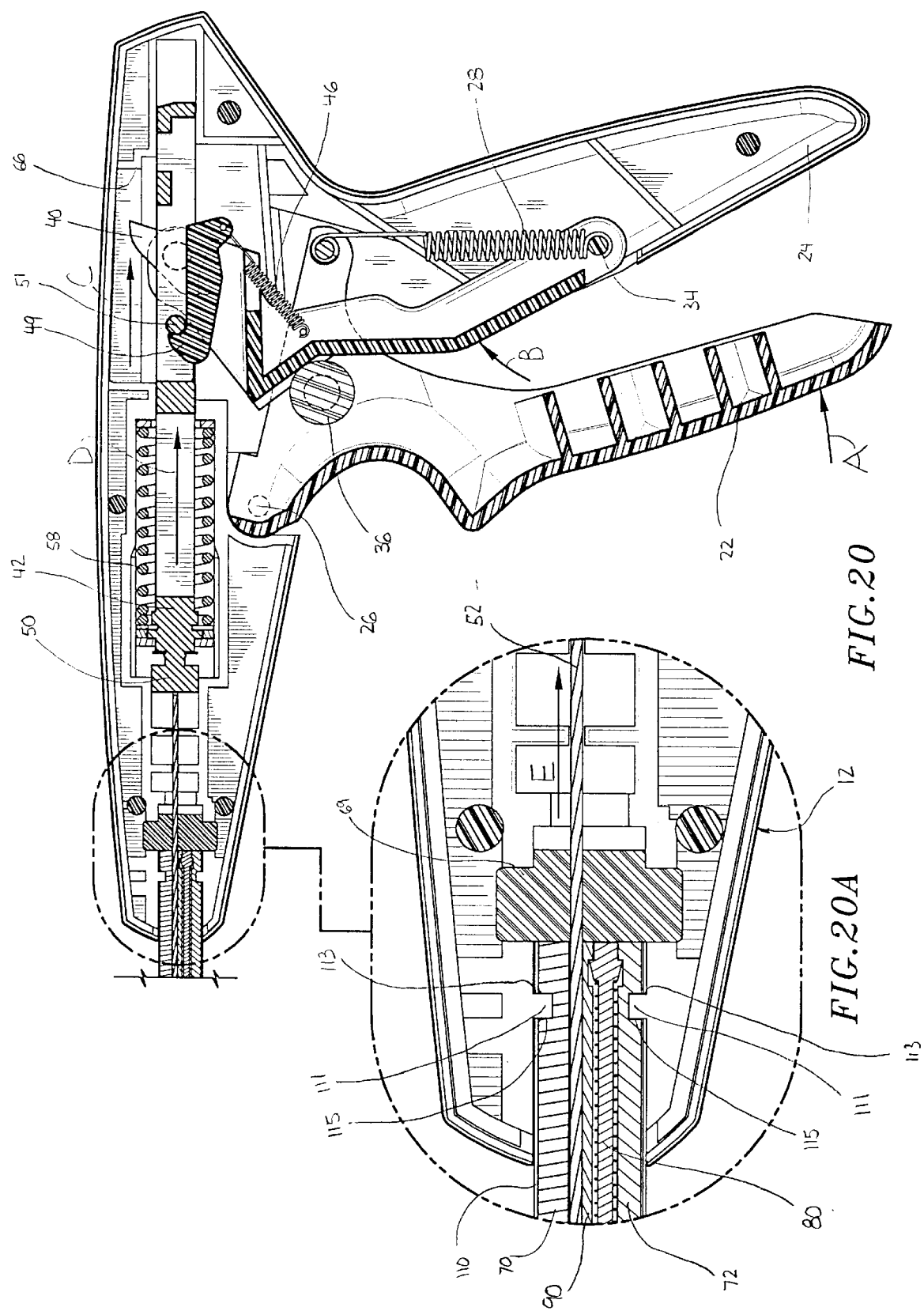
FIG. 20 is a side cross-sectional view of the proximal end of the embodiment shown in FIG. 1 in a partially actuated position.
FIG. 20A is an enlarged view of the indicated area of detail of FIG. 20.

FIGS. 20 to 20c illustrate the device in a partially actuated position with the movable handle 22 partially rotated about pivot pin 26 in the direction indicated by arrow "A". Rotation of movable handle 22 effects movement of cam roller member 36 into engagement with actuation arm member 32 along cam path 38 to rotate actuation arm member 32 about pivot pin 34 in the direction indicated by arrow "B". Movement of actuation arm member 32 causes movement of latch member 40 in the direction indicated by arrow "C" to slide the firing block 42 proximally in the direction indicated by arrow "D". As best illustrated in FIG. 20B, proximal movement of the firing block 42 causes proximal movement of the firing bar 52 as indicated by arrow "E". As the firing bar 52 travels over the fastener retainer 102, the fastener retainer 102, no longer deflected, returns to a position obstructing the path of travel of the series of fasteners 31 over the ramp surface 75.

FIGS. 21–21C illustrate the device an instant prior to being moved to the fully actuated position. As illustrated in FIG. 21, the movable handle 22 has been rotated almost into engagement with stationary handle 24 as indicated by arrow "A" effecting proximal movement of the latch member 40 and the firing block 42, as indicated by arrows "C" and "D", respectively. Upon engagement of the latch member 40 with camming wall 66, the latch member 40 is rotated in the direction indicated by arrow "F" to disengage the hook member 49 from the post member 51 to permit the compression spring 58 to drive the firing block 42 and firing bar 52 distally.

An instant before reaching the fully actuated position, the firing bar 52 has moved to an almost fully retracted position, as indicated by arrow "E". Referring to FIGS. 21B–21C, once the firing bar 52 has been retracted beyond engagement with leaf spring 94, the leaf spring 94 returns to its undeflected position, no longer obstructing the travel path of the fastener, to allow the distal-most fastener to move up the ramp 75. The distal-most fastener 30 moves distally, as indicated by arrow "F", until the suture portion 124 of the fastener 30 engages the fastener retainer 102 to retain fastener 30 in position to be engaged by firing bar 52. The series of fasteners 31 move distally in the direction indicated by arrow "G" behind distal-most fastener 30. With post member 51 released from latch member 40, firing block 42 is driven distally by compression spring 58. Firing block 42 thus drives firing bar 52 distally so that tabs 116 at the distal end of firing bar 52 engage the proximal end of distal-most fastener 30 to eject the fastener from the distal end of the elongated body portion of the device.

Figure 22:
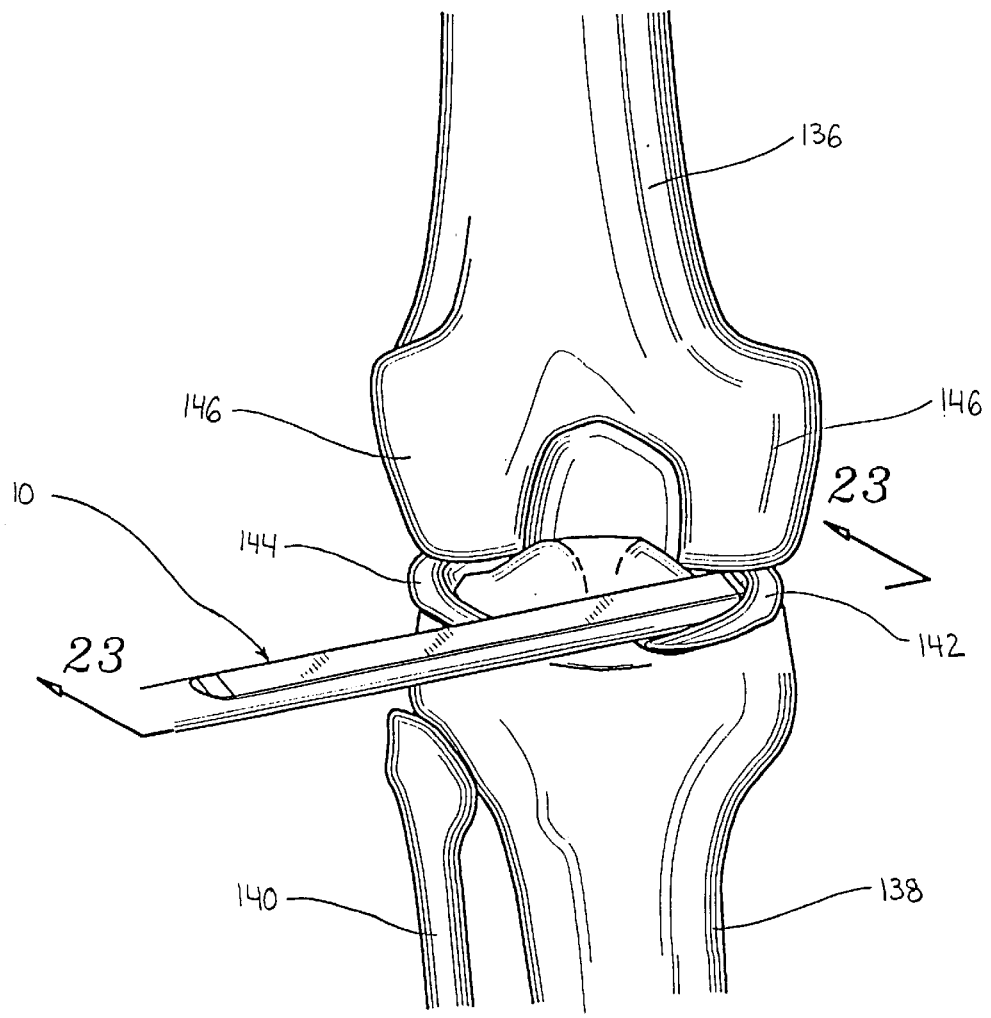
FIG. 22 is a front view of the knee joint with the device of the embodiment shown in FIG. 1 inserted into the knee joint.
Figure 23:
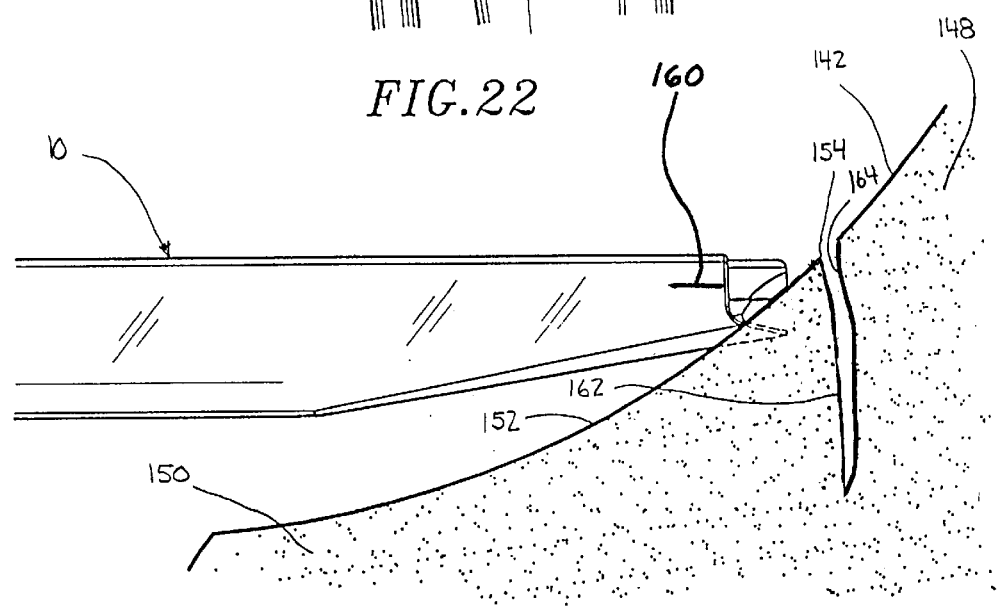
FIG. 23 is a cross-sectional view taken along section line 23—23 of FIG. 22.

FIGS. 22 and 23 illustrate a simplified view of the structure of the knee, including the pertinent components of the knee to which this disclosure is directed. As is well known, the femur 136 is joined to the tibia 138 and fibula 140 by muscles, tendons and ligaments (not shown). These bones are separated by menisci 142 and 144. The menisci 142 and 144 are crescent shaped and include a thick outer periphery 148 that slopes downward to a thin inner periphery 150. Condyles 146 of femur 136 rest on the inner sloping surface 152 of the menisci, thus rendering the surface susceptible to tears forming in the tissue, such as a tear 154.

The damaged or torn meniscus 142 in the knee is arthroscopically approached from the front of the knee by inserting the elongated body portion 14 of the device 10 into the joint capsule of the knee, such as by inserting elongated body portion 14 through a cannula. The distal end of the device 10 is positioned such that the anchors 120 and 122 of the fastener 30 will extend through both walls 162 and 164 of the tear 154 in the meniscus and remain embedded in the tissue behind wall 164. If the meniscus tissue requires repositioning prior to repairing the tear 154, this is accomplished by inserting a barb 112 into the tissue and moving the tissue to its proper position. This may be required when tissue on opposite sides of the tear are separated. After the meniscus tissue has been repositioned and the device has been properly positioned for firing using the fastener locator indicia 160 as a guide, barbs 112 are engaged with the tissue adjacent the tear 154. Because of the tapered end 114 of the lower housing 72, the device 10 can be positioned substantially flush against the meniscus tissue having the tear 154 while preserving visibility of the site. The device 10 is actuated to insert a fastener 30 into the tissue so that the suture 124 is substantially flush with the meniscus tissue and the tear 154 is maintained in an abutting relationship. The procedure detailed above is repeated as necessary to effect the desired repair of the torn tissue.

A procedure for repairing meniscal tears is also envisioned in which anchors 120 and 122 are inserted into the meniscus on opposite sides of the tear, such that the suture extends across the tear.

It will be understood that various modifications may be made to the embodiment disclosed herein. For example, the handle assembly disclosed may be replaced by other known assemblies capable of reciprocating the firing bar 52 in the manner required to effect ejection of the fasteners. Therefore, the above description should not be construed as limiting, but merely as exemplifications of preferred embodiments. Those skilled in the art will envision other modification within the scope and spirit of the claims appended hereto.

What is claimed is:

1. An anvilless fastener applying device, comprising:
   a handle mechanism;
   an elongated body portion extending from the handle mechanism having a proximal end and a distal end;
   a series of fasteners supported within the elongated body portion in tip-to-tail fashion, each fastener having a pair of legs joined by a flexible connecting member;
   a firing bar having first and second tabs extending from a distal end thereof, the firing bar being operatively connected to the handle mechanism and being movable to move the first and second tabs into engagement with the legs of a distal-most fastener of the series of fasteners to eject the distal-most fastener from the distal end of the elongated body portion into tissue; and
   the elongated body portion including a support casing having a cylindrical proximal cross-section tapering to a distal cross-section having planar top and bottom surfaces.

2. A device according to claim 1 wherein the support casing is constructed from stainless steel.

3. A device according to claim 1 wherein the distal end of the elongated body portion includes a tapered distal face positioned to engage tissue, the tapered distal face extending through the distal end of the support casing.

4. A device according to claim 1 further comprising a fastener supply mechanism including a follower member positioned proximal of the proximal-most fastener of the series of fasteners and a biasing member biasing the follower member into engagement with the proximal most fastener to advance the series of fasteners distally.

5. A device according to claim 4 wherein the elongated body portion includes first and second longitudinal tracks extending through the length of the elongated body portion, the first and second tracks being separated by an elongated cover plate, and wherein the fastener supply mechanism and the series of fasteners are movably positioned within the first track and the firing bar is movably positioned within the second track.

6. A device according to claim 5 wherein the distal end of the elongated body portion adjacent the first track includes a ramp surface, the ramp surface merging the first and second tracks into a single merged track having a longitudinal axis aligned with a longitudinal axis of the second track.

7. A device according to claim 6 further comprising a retainer member secured in the distal end of the body portion and being movable from a first position retaining the distal-most fastener at least partially within the merged track to a second position permitting the distal-most fastener to travel from the merged track.

8. A device according to claim 7 further comprising a leaf spring positioned adjacent the ramp surface, the leaf spring being movable from a first position obstructing fastener movement over the ramp surface to a second position spaced from the ramp surface.

9. A fastener applying device, comprising:
   a handle mechanism;
   an elongated body portion extending from the handle mechanism having a proximal end and a distal end;
   a series of fasteners supported within the elongated body portion in tip-to-tail fashion, each fastener having a pair of legs joined by a flexible connecting member;
   a firing bar operatively connected to the handle mechanism and being movable to engage a distal-most fastener of the series of fasteners and eject the distal-most fastener from the distal end of the elongated body portion;
   at least one barb extending distally from the distal end of the elongated body portion; and
   the elongated body portion including a support casing having a cylindrical proximal cross-section tapering to a distal cross-section having planar top and bottom surfaces.

10. An anvilless fastener applying device, comprising:
    a handle assembly;
    an elongated body portion extending from the handle assembly, the elongated body portion having a distal face positioned to engage body tissue;

a series of fasteners supported in tip-to-tail fashion along the longitudinal axis of the elongated body portion each fastener having a pair of legs connected by a flexible connecting member;

a firing bar operatively connected to the handle assembly and being movable to engage a distal-most fastener of the series of fasteners and eject the distal-most fastener from the distal end of the elongated body portion adjacent the distal face; and wherein the distal face of the elongated body portion positioned to engage tissue is tapered.

11. A device according to claim 10 wherein the elongated body portion comprises a support casing having a cylindrical proximal cross-section tapering to a distal cross-section having planar top and bottom surfaces.

12. A device according to claim 10 further comprising at least one barb extending distally from the distal end of the device.

13. A device according to claim 12 wherein the at least one barb includes two barbs, wherein the barbs are positioned on opposite sides of the elongated body portion.

14. A device according to claim 11 wherein the elongated body portion further includes an inner housing positioned within the support casing, the inner housing having a distal end extending through a distal end of the support casing, and wherein the tapered distal face of the elongated body portion is formed on the distal end of the inner housing.

15. A fastener applying device, comprising:

a handle assembly;

an elongated body portion extending from the handle assembly;

a series of fasteners supported in tip-to-tail fashion along the longitudinal axis of the elongated body portion, each fastener including a first and a second anchor member interconnected by a flexible member;

a firing bar operatively connected to the handle assembly and being movable to engage the first and second anchor members of a distal-most fastener of the series of fasteners and eject the distal-most fastener from the elongated body portion; and at least one barb fixedly positioned on a distal end of the elongated body portion and extending distally therefrom.

16. A device according to claim 15 wherein the at least one barb includes two barbs, the barbs being spaced on opposite sides of the elongated body portion.

17. A method for repairing meniscal tears in a human joint comprising:

providing a fastener applying device having a handle mechanism, an elongated body portion extending distally from the handle mechanism and including a tapered distal face, a series of fasteners supported within the body portion, and at least one barb fixedly positioned on the distal end of the elongated body portion and extending distally therefrom;

inserting the elongated body portion into a human joint adjacent to a tear in meniscal tissue;

positioning the device relative to side walls of the tear using the at least one barb and positioning the tapered distal face against the meniscus tissue; and actuating the fastener applying device to eject a fastener from the elongated body portion into the tissue adjacent the tear.

18. A method according to claim 17, wherein each fastener of the series of fasteners includes a pair of legs joined together by a flexible member and further including the step of positioning the fastener device to eject the fastener such that each leg passes through the walls of the tear and remains embedded in tissue behind the tear.

19. A method for repairing meniscal tears in a human joint comprising:

providing an anvilless fastener applying device having a handle mechanism, an elongated body portion extending distally from the handle mechanism, a series of fasteners supported within the body portion in tip-to-tail fashion, each fastener having a pair of legs joined by a flexible connecting member, at least one barb extending from the distal end of the elongated body portion, fastener locator indicia on the distal end of the elongated body portion identifying the point of ejection of the fasteners from the device, and a firing bar operatively connected to the handle mechanism to eject a distal-most fastener of the series of fasteners upon actuation of the handle mechanism;

inserting the elongated body portion into a human joint adjacent to tissue requiring repair;

positioning the device relative to the tissue within the joint to a desired position using the at least one barb and the fastener locator indicia; and actuating the handle mechanism to eject a fastener from the elongated body portion into the tissue.

20. An anvilless fastener applying device, comprising:

a handle assembly;

an elongated body portion extending distally from the handle assembly;

a series of fasteners supported in tip-to-tail fashion along the longitudinal axis of the elongated body portion, each fastener having a first and a second anchor member connected together by a suture member; and a firing bar operatively connected to the handle assembly and being movable to engage a distalmost fastener of the series of fasteners and eject the distalmost fastener from the distal end of the elongated body portion to simultaneously advance the first and second anchor.

21. An anvilless fastener applying device according to claim 20 wherein each of the anchor members includes a proximal end, the suture joining the proximal ends of the anchor members.

22. An anvilless fastener applying device according to claim 21 wherein the proximal end of each of the anchor members includes a notch, the notch being positioned to receive the distal end of one of the anchor members of a proximally positioned fastener in the series of fasteners.

* * * * *